(12) United States Patent
Alsarhan

(10) Patent No.: US 10,646,243 B1
(45) Date of Patent: May 12, 2020

(54) MAXILLARY FRENUM CLAMPING TOOL

(71) Applicant: KING SAUD UNIVERSITY, Riyadh (SA)

(72) Inventor: Mohammed Abdullah Alsarhan, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/566,848

(22) Filed: Sep. 10, 2019

(51) Int. Cl.
*A61B 17/24* (2006.01)
*A61B 17/28* (2006.01)
*A61B 17/04* (2006.01)
*A61C 3/00* (2006.01)

(52) U.S. Cl.
CPC .......... *A61B 17/24* (2013.01); *A61B 17/0483* (2013.01); *A61B 17/2816* (2013.01); *A61B 17/2833* (2013.01); *A61C 3/00* (2013.01); *A61B 2017/2808* (2013.01); *A61B 2017/2837* (2013.01)

(58) Field of Classification Search
CPC ... A61B 17/0483; A61B 17/062; A61B 17/24; A61B 17/2816; A61B 17/282; A61B 17/2833; A61B 2017/2808; A61B 2017/2837
USPC ................................................ 606/148, 207
See application file for complete search history.

(56) References Cited

U.S. PATENT DOCUMENTS

| 3,364,933 A | 1/1968 | Leopold |
| 3,823,719 A | 7/1974 | Cummings |
| 4,655,223 A * | 4/1987 | Kim ..................... A61B 17/282 606/148 |
| 5,059,214 A | 10/1991 | Akopov et al. |
| 5,133,737 A | 7/1992 | Grismer |
| 5,251,642 A | 10/1993 | Handlos |
| 9,237,899 B2 | 1/2016 | Ray |
| 2008/0172085 A1 * | 7/2008 | Chiu .................. A61B 17/0482 606/205 |
| 2014/0046363 A1 | 2/2014 | Frimand Ronnow |

FOREIGN PATENT DOCUMENTS

DE 424807 C 2/1926

* cited by examiner

*Primary Examiner* — Martin T Ton
(74) *Attorney, Agent, or Firm* — Richard C. Litman; Nath, Goldberg & Meyer

(57) ABSTRACT

The maxillary frenum clamping tool includes two articulating members, each of the members having a clamping end and a gripping end. The clamping ends of the articulating members are curved to retract the upper lip while clamping the maxillary labial frenum and have blunt tips to minimize damage to the surrounding tissue. Immediately below the blunt tips, each member defines a jaw section having a serrated inner edge. The outer edges of the jaw sections define guide indentations for guiding a curved suture needle. The gripping end of each member defines a finger loop and part of a ratcheting lock mechanism for locking the members at set positions. During use, the clamping too may be used to clamp the maxillary frenum with the jaw portions so that the clamped tissue can be easily sutured using the guide indentations.

7 Claims, 6 Drawing Sheets

MAXILLARY FRENUM CLAMPING TOOL

BACKGROUND

1. Field

The disclosure of the present patent application relates to maxillary frenum removal and reduction, and particularly to a maxillary frenum clamping tool for clamping the maxillary frenum while performing a removal or reduction procedure.

2. Description of the Related Art

The maxillary frenum is a fold of mucous membrane, usually with enclosed muscle fibers, that attaches the upper lip and cheeks to the alveolar mucosa and/or gingiva and underlying periosteum. There are different variations of frenum attachments found in individual patients. Frena fibers may be found to attach in the vestibular depth of the maxillary arch within the mucosa, above the mucogingival junction, reaching the attached gingiva, and extending beyond toward the papillary gingiva and the palate.

A frenum becomes a problem if the attachment is too close to the marginal gingiva. This anatomic situation may be a genetic condition of the individual or the result of recession of the gingival margin reaching the area of the frenum. A hypertrophic frenum may also be involved in the etiology of the midline diastema (gap) of the maxillary central incisors, leading to esthetic complications in young patients. Also, tension on the frenum may pull the gingival margin away from the tooth. This condition may be conducive to plaque accumulation and inhibit proper placement of the toothbrush at the gingival margin.

Different surgical options can be performed to reduce and/or remove advanced frenum attachments. Frenectomy, is the complete removal of the frenum, including its attachment to underlying bone, and may be required in the correction of an abnormal diastema between the maxillary central incisors. Frenotomy, is the relocation of the frenum, usually in a more apical position. Both procedures may be done as additional steps during periodontal plastic procedures (e.g., free gingival graft), but most of the time they are accomplished as separate procedures.

Traditionally, this procedure can be done using a surgical hemostat to hold the frenum deep into the vestibular depth. During these procedures, an incision is made using a blade that follows the outer line of the hemostat to dissect the frenum from its underlying attachment. After cleaning the site from any remnants or attachments, suturing is accomplished to approximate wound edges, control bleeding, and stabilize gingival tissues. The classical technique is considered invasive due to the deep cuts into the oral tissues reaching the alveolar bone to remove any remnants of fibers. Also, bleeding is spontaneous and sometimes bothersome to surgeons, since it affects their field of view.

An alternative to the classical frenectomy/frenotomy procedure is achieved by using electrosurgery, especially for patients with a bleeding tendency. Recently, the advent of lasers in soft tissue procedures facilitates less operating time and rapid wound healing with instant hemostasis. Both techniques may be done without sutures. However, suturing plays a role in minimizing scar tissue formation, which may be an esthetic concern, especially in patients with a high-smile line.

There are many forceps known in the art that have been used to hold reduced maxillary frenum flaps together for suturing. However, traditional forceps can easily damage surrounding tissue, resulting in possible further complications. In addition, it is difficult to suture the flaps together when they are held by a traditional forceps, since they do not accommodate a curved suture needle.

Thus, a maxillary frenum clamping tool solving the aforementioned problems is desired.

SUMMARY

The maxillary frenum clamping tool includes two articulating members, each of the members having a clamping end and a gripping end. The clamping ends of the articulating members are curved to retract the upper lip while clamping the maxillary labial frenum and have blunt tips to minimize damage to the surrounding tissue. Immediately below the blunt tips, each member defines a jaw section having a serrated inner edge. The outer edges of the jaw sections define guide indentations for guiding a curved suture needle. The gripping end of each member defines a finger loop and part of a ratcheting lock mechanism for locking the members at set positions. During use, the clamping tool may be used to clamp the maxillary frenum with the jaw portions so that the clamped tissue can be easily sutured using the guide indentations.

The articulating members are pivotally attached medially between the clamping ends and the gripping ends so that the tool may be gripped by the finger loops to pivot the clamping ends towards each other and away from each other in the manner of a scissors. However, unlike a scissors, the blades or shanks do not overlap when pivoted towards each other. The jaw sections of the articulating members are substantially parallel when pivoted towards each other and have serrated edges that mesh for firmly gripping the tissue of the frenum, and can be locked in that position by the ratcheting lock mechanism, similar to a hemostat. The blunt tips have an arcuate curve, arching at least partially back in the same direction towards the finger loops so that the inner lip is retracted and supported above the frenum when the tool clamps the frenum. The indentations in the jaw sections may define a sequence or series of undulating recesses for guiding a curved suture needle used to suture the mucosa or the folds of the frenum during a procedure to remove or repair the frenum.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The maxillary frenum clamping tool includes two articulating members, each of the members having a clamping end and a gripping end. The clamping ends of the articulating members are curved to retract the upper lip while clamping the maxillary labial frenum and have blunt tips to minimize damage to the surrounding tissue. Immediately below the blunt tips, each member defines a jaw section having a serrated inner edge. The outer edges of the jaw sections define guide indentations for guiding a curved suture needle. The gripping end of each member defines a finger loop and part of a ratcheting lock mechanism for locking the members at set positions. During use, the clamping tool may be used to clamp the maxillary frenum with the jaw portions so that the clamped tissue can be easily sutured using the guide indentations. The tool is preferably made from stainless steel.

For explanatory purposes during the following disclosure, the direction in which the clamping arms curve is considered up, an open configuration is when the clamping portions are not contacting each other, and the inside of the members is the surface facing the opposing member.

Figure 1:
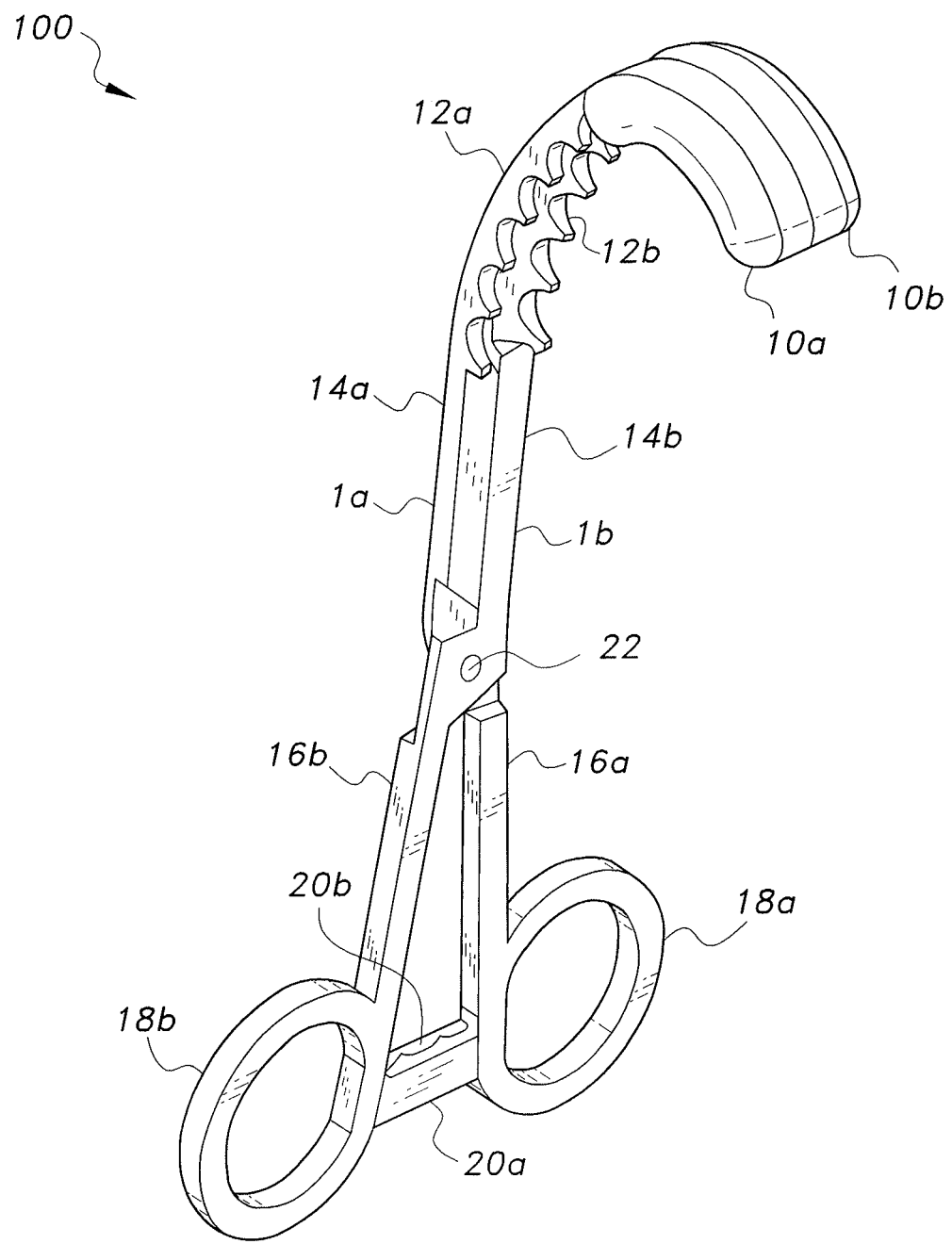
FIG. 1 is a perspective view of a maxillary frenum clamping tool.

FIGS. 1-5 show an embodiment of the maxillary frenum clamping tool 100. As seen in FIG. 1, a hinge pin 22 connects a first member 1a and a second member 1b to provide an articulating tool. The first member 1a and the second member 1b each have a central cross-over pivot plate, the pivot plates being disposed one above the other, the hinge pin 22 extending centrally through the overlapping cross-over pivot plates. Each member 1a, 1b has a lower shank extending downward from one side of the cross-over plate and terminating in a finger grip or finger loop 18a, 18b, and an upper shank extending upward from the opposite side of the cross-over plate, the upper shanks defining a clamping end of the members 1a, 1b. The upper shanks are attached to the cross-over plate so that the upper shanks are parallel to and abut each other when the first and second members are pivoted on the hinge pin to approximate the upper shanks in a closed or clamping position, while the lower shanks extend obliquely downward and are separated from each other with the tool in the clamping position. When the finger loops 18a, 18 b are used to grip and separate the lower shanks farther apart, the upper shanks pivot away from each other to an open position.

The clamping end of each member 1a, 1b may be divided into three portions, which include a blunt tip 10a, 10b at the terminal end, a central jaw portion 12a, 12b, and an extension portion 14a, 14b spanning from the hinge pin 22 to the jaw portion 12a, 12b. Each member 1a, 1b is curved upward from the jaw section 12a, 12b through the blunt tip 10a, 10b, so that the tip 10a, 10b curves back generally toward the gripping section. The blunt tips 10a, 10b may have planar inner surfaces 11a, 11b (shown in FIG. 5) designed to bear against each other when the tool 100 is in a closed configuration. An outer surface of the blunt tips 10a, 10b defines a bulbous shape or has rounded edges designed to minimize damage to contacted tissue.

The jaw sections 12a, 12b of the members 1a, 1b include serrations 30a, 30b on their lower inner edge. The serrations 30a, 30b extend towards the opposing member 1a or 1b so that the jaw sections 12a, 12b securely grip any tissue pinched between the members 1a, 1b when they are clamped together. The upper outer edge of each jaw portion 12a, 12b defines multiple guide protrusions 32a, 32b (see FIG. 4A) and associated guide valleys or indentations 34a, 34b running along a length of the jaw portion 12a, 12b. The guide protrusions 32a, 32b and valleys 34a, 34b are equally shaped and sized to provide guides, which can be used for aligning a needle when suturing tissue clamped between the jaw portions 12a, 12b. The serrations 30a, 30b are disposed lower than the guide protrusions 32a, 32b and the guide indentations 34a, 34b so that the clamping edge does not interfere with the needle guides.

The extension portion 14a, 14b may extend linearly out from the hinge pin 22 to provide separation between the jaws portions 12a, 12b and the pin 22. In some embodiments, one clamping end 10a, 12a, 14a may mirror the other clamping end 10b, 12b, 14b.

Each member 1a, 1b may define a finger loop 18a, 18b at the gripping end of the member 1a, 1b, which may be separated from the hinge pin 22 by a separating member 16a, 16b. A locking member 20a, 20b (the locking members are overlapping plates with interlocking ratchet teeth, as known in the art; such members are conventional and well known in surgical clamps, and need not be described further) may be attached to a side of each finger loop 18a, 18b. When the clamping tool is closed, a bottom surface of one locking member 20a may be contacted with a top surface of the opposing locking member 20b. The contacting surface may define teeth that interlock to lock the members 1a, 1b at set positions. The lock provided by the locking members 20a, 20b may be broken by separating the surfaces.

Figures 2A, 2B:
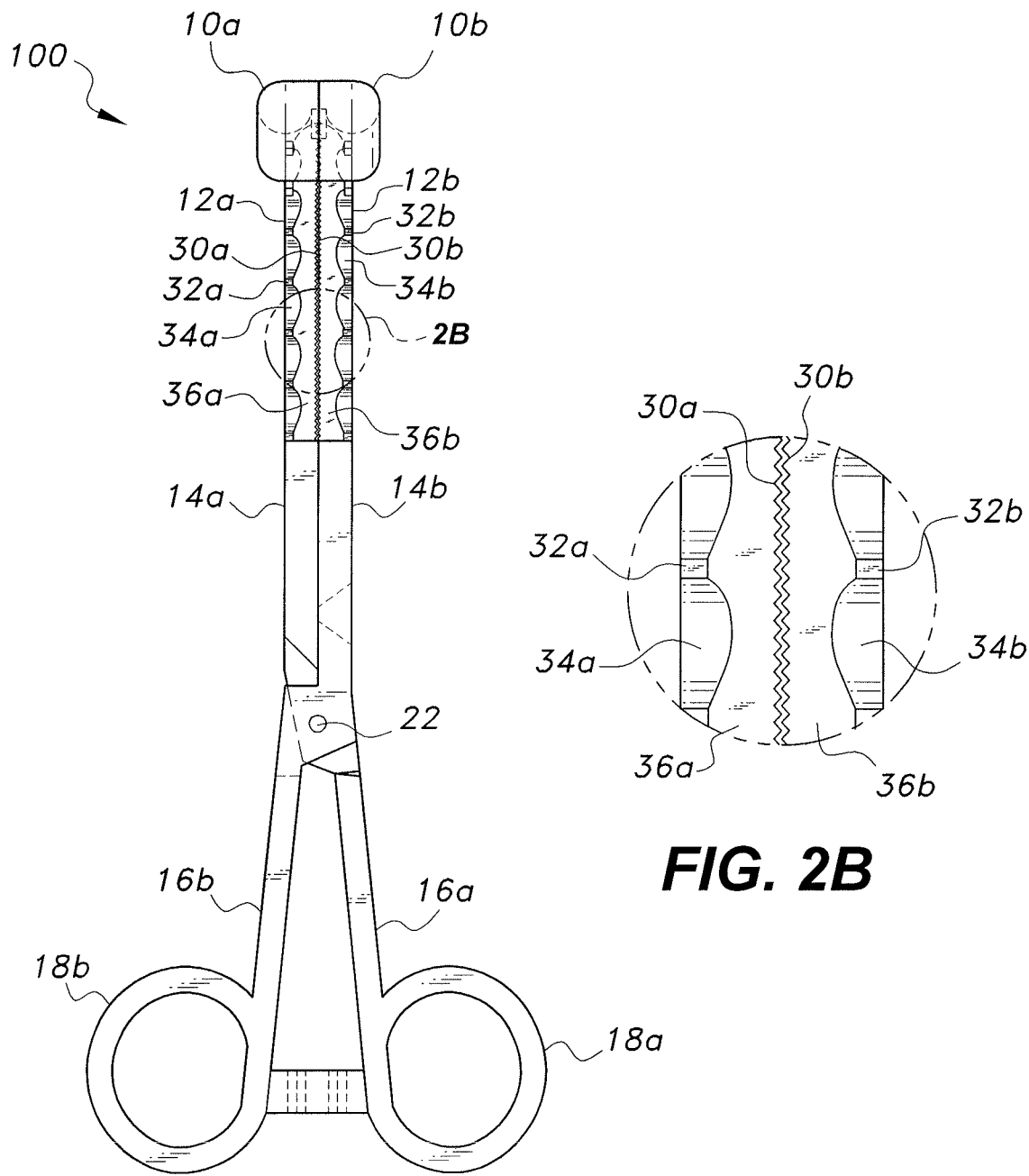
FIG. 2A is a top view the maxillary frenum clamping tool of FIG. 1.
FIG. 2B is a detailed top view of area 2B of FIG. 2A.

FIGS. 2A-2B show top views of the clamping tool 100. As seen in FIGS. 2A-2B a face 36a, 36b is defined between the guide projections 32a, 32b and the serrated edge 30a, 30b of each jaw portion 12a, 12b, i.e., the guides 32a, 32b extend from the upper surface of the corresponding members 1a, 1b, but are positioned along the outer edge of the member 1a, 1b, leaving the faces 36a, 36b. In some embodiments, the face 36a, 36b may have a concave curvature. The concave curvature allows room for a curved suture needle 40 to pierce the clamped tissue 50 at a proper depth (see FIGS. 4A-4C). For example, when suturing, a practitioner can place the needle 40 between two adjacent alignment projections 32a and then allow the needle to follow the surfaces 36a, 36b to ensure the needle 40 is piercing the clamped tissue 50 at the proper depth.

Figure 3A:
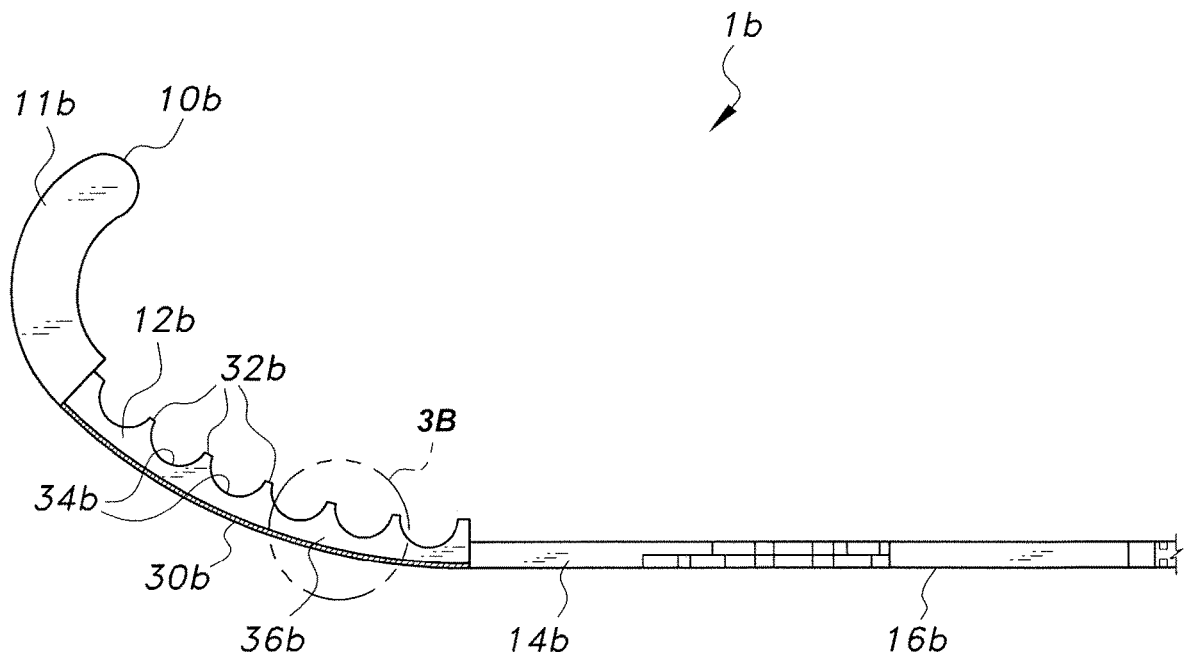
FIG. 3A is a side view of one of the articulating members of the maxillary frenum clamping tool.
Figure 3B:
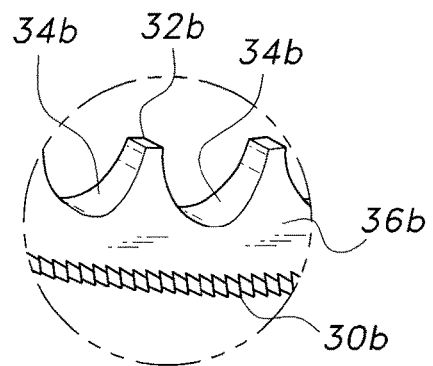
FIG. 3B is a detailed perspective view of area 3B of FIG. 3A.

FIGS. 3A-3B show the inside surface of the second member 1b, which in some cases will mirror the opposing first member 1a. As previously discussed, the lower inside edge of the jaw 12b defines serrations 30b and the upper outside edge defines evenly spaced alignment projections 32b and valleys 34b along its length. FIG. 3B shows the concave face 36b spanning from the serrations 30b to the alignment projections 32b for guiding a suture needle 40.

Figure 4A:
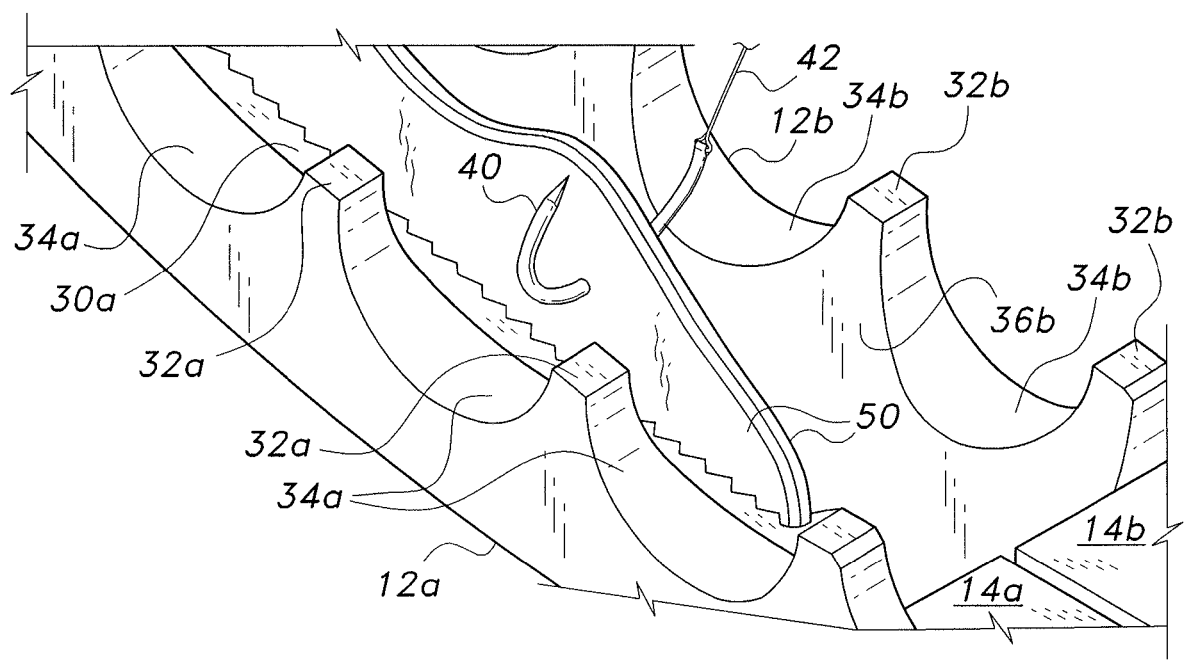
FIG. 4A is a partial environmental perspective view of the maxillary frenum clamping tool of FIG. 1A, shown clamping maxillary frenum flaps and with a suture needle in the process of suturing the flaps together.
Figure 4B:
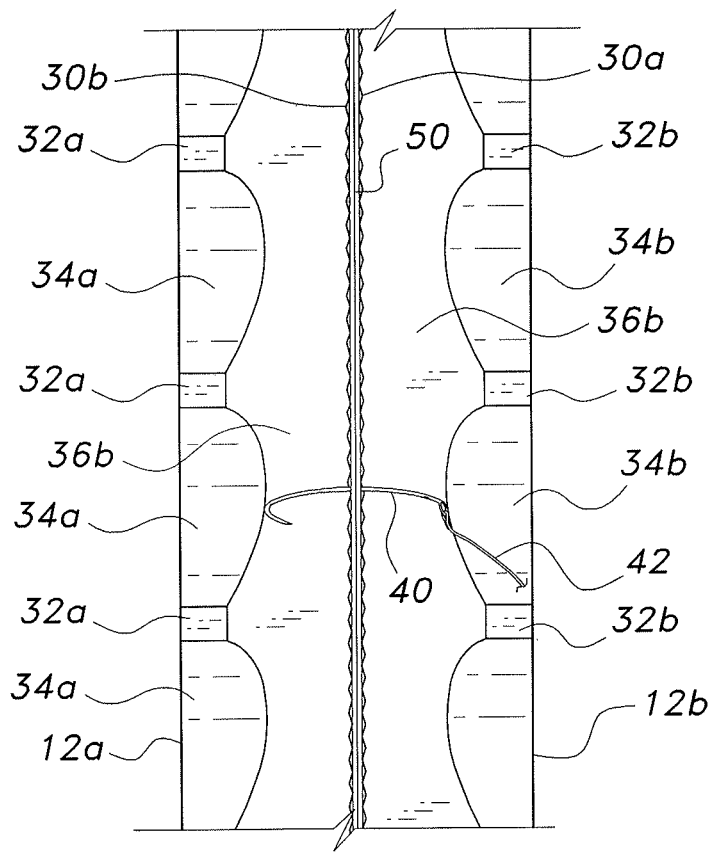
FIG. 4B is a partial environmental top view of the maxillary frenum clamping tool, shown clamping maxillary frenum flaps and with a suture needle in the process of suturing the flaps together.
Figure 4C:
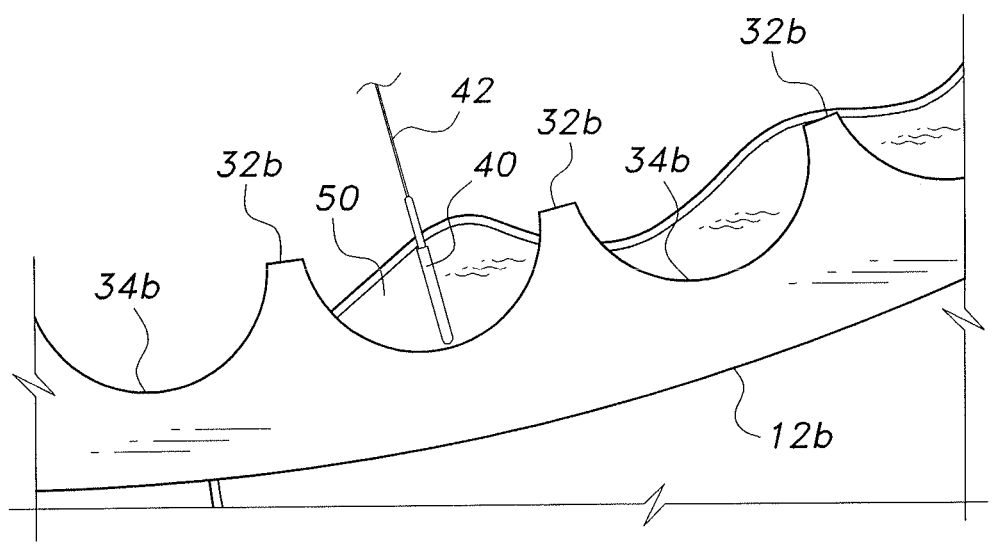
FIG. 4C is a detailed partial environmental perspective of the maxillary frenum clamping tool, shown clamping maxillary frenum flaps and with a suture needle in the process of suturing the flaps together.

FIGS. 4A-4C show how the guide valleys 34a, 34b can be used to guide a curved suture needle 40. As seen in FIG. 4A, two flaps of tissue 50, such as a reduced maxillary frenum, are clamped together by the jaw portions 12a, 12b of the clamping tool 100. A practitioner may align the needle 40 with aligned guide valleys 34a, 34b to ensure that sutures 42 are evenly spaced and placed at a consistent depth. FIGS. 4B-4C show a top and side view, respectively, of the suture needle 40 being aligned with the aligned guide valleys 34*a*, 34*b*. As seen in FIGS. 4A-4C, the suture needle 40 is aligned with the midpoint of the aligned valleys 34*a*, 34*b*, which controls alignment between the sutures 42 and the depth of the suture 42. The medical practitioner may then proceed to apply sutures 42 at each set of aligned valleys 34*a*, 34*b* necessary for the procedure. As a result, the practitioner will easily be able to provide sutures 42 with proper spacing and depth in a difficult to operate area. The precise placement of sutures 42 may provide more secure wound closure with minimal tension on the margins of the flaps 50 being connected. In addition, the guide valleys 34*ab*, and adjacent faces 36*a,b* will help shield the surrounding tissue from the tip of the needle 40, which is capable of causing unintended tissue damage.

Figure 5:
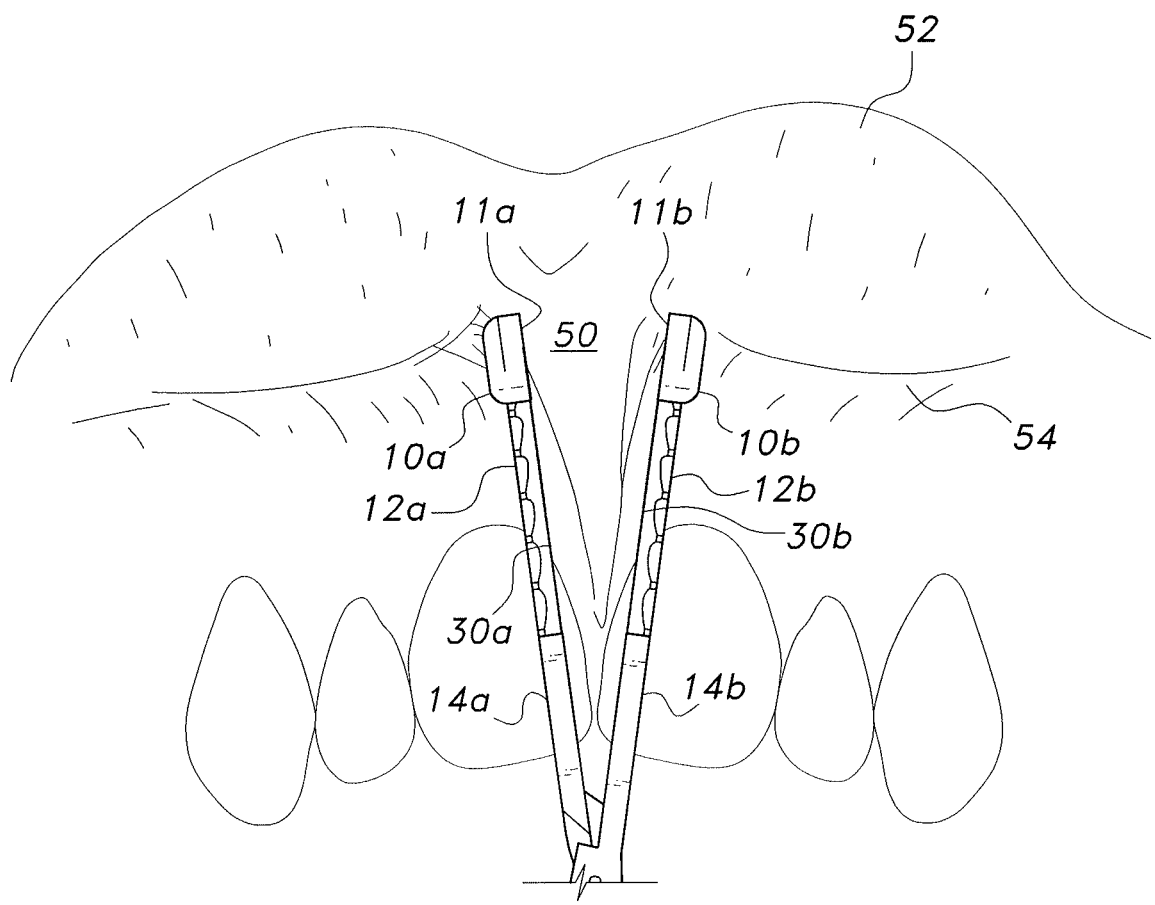
FIG. 5 is an environmental perspective view of the maxillary frenum clamping tool, shown retracting a patient's upper lip and just prior to clamping the maxillary frenum.

FIG. 5 shows the clamping tool 100 being used to clamp a maxillary frenum 50. As seen in FIG. 5, the maxillary frenum 50 of a patient is placed between the jaw portions 12*a*, 12*b* of the first member 1*a* and second member 2*b*. The blunt tips 10*a*, 10*b* reside against the intersection between the labial frenum 54 and the upper lip 52, so that the curve of the tips 10*a*, 10*b* accommodates the curve in the tissue for minimal discomfort to the patient while retracting the upper lip 52. The jaw portions 12*a*, 12*b* extend along a length of the maxillary frenum 50. When the jaw portions 12*a*, 12*b* are approximated, they can clamp and secure the maxillary frenum 50 for a removal or reduction procedure.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A maxillary frenum clamping tool, comprising:
   first and second articulating members, each of the members having:
   a central pivot plate, the pivot plates each having opposing lateral sides, the pivot plates being pivotally disposed one above the other;
   a lower shank extending downward from one side of the pivot plate, the lower shank having a terminal end and a finger loop defined at the terminal end; and
   an upper shank extending upward from the opposite side of the pivot plate, the upper shanks of the first and second members extending parallel to and abutting each other when the first and second members are pivoted to approximate the upper shanks in a clamping position, the lower shanks being spaced apart and extending obliquely away from each other in the clamped position, the first and second members being pivotal to an open position in which the upper shanks separate from each other, the upper shanks each having a blunt tip end at a distal end of each upper shank, each blunt tip end including a distal end, a proximal end, an inner surface, and being arcuately curved parallel to each other between the distal end of the blunt tip end and the proximal end of the blunt tip end, wherein the inner surfaces of each of the blunt tip ends defines a planar surface, the blunt tip ends being adapted for retracting a patient's upper lip above the patient's maxillary labial frenum in the clamping position;
   a hinge pin extending centrally through the overlapping pivot plates to pivotally attach the first and second articulating members;
   a clamping jaw section defined on the upper shanks of the first and second articulating members, the clamping jaw section being disposed between the hinge pin and the proximal end of the blunt tip end, the clamping jaw section including:
   a serrated edge, the serrated edge extending below the blunt tip end and being solely disposed on the clamping jaw section, the serrated edges of the first and second articulating members meshing when the first and second members are pivoted to approximate the upper shanks in a clamping position; and
   a plurality of guides extending in series opposite the serrated edge, the guides being adapted for guiding a curved suture needle when suturing folds of the maxillary labial frenum, the plurality of guides comprises an alternating series of projections and arcuate indentations defining a continuous scalloped formation, wherein the projections and arcuate indentations of the plurality of guides disposed on the first articulating member are aligned with the projections and arcuate indentations of the plurality of guides disposed on the second articulating member; and
   a first lock plate and a second lock plate extending from the lower shanks of the first and second articulating members, respectively, the lock plates overlapping and having selectively interlocking ratcheting teeth in order to selectively lock the first and second articulating members in the clamping position with folds of the maxillary labial frenum clamped between the serrated edges of the clamping jaw sections of the upper shanks.

2. The maxillary frenum clamping tool according to claim 1, wherein the serrated edge of each of the clamping jaw sections is disposed lower than the opposing plurality of guides.

3. The maxillary frenum clamping tool according to claim 1, wherein the upper shank of each of the first and second articulating members defines a face extending between the serrated edge and the opposing plurality of guides.

4. The maxillary frenum clamping tool according to claim 3, wherein said face is concave.

5. The maxillary frenum clamping tool according to claim 1, wherein the blunt tip end of each of the upper shanks has a planar face, the planar faces of the blunt tip ends abutting each other when the first and second articulating members are pivoted to the clamping position.

6. The maxillary frenum clamping tool according to claim 1, wherein the blunt tip end of each of the upper shanks has rounded edges adapted for reducing tears in mucosal tissue when the blunt tip ends retract the patient's upper lip to expose the maxillary labial frenum.

7. The maxillary frenum clamping tool according to claim 1, wherein the tool is made from stainless steel.

* * * * *